United States Patent
Pyro et al.

(10) Patent No.: US 12,059,205 B2
(45) Date of Patent: Aug. 13, 2024

(54) REVERSE RETROPULSION LITHOTRIPSY DEVICE

(71) Applicant: GYRUS ACMI, INC., Southborough, MA (US)

(72) Inventors: Jan T. Pyro, Shrewsbury, MA (US);
Charles Baker, Rogers, MN (US);
Lucie Freedman, Champlin, MN (US);
Sergey A. Bukesov, Acton, MA (US);
Peter J. Crowley, Norfolk, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 591 days.

(21) Appl. No.: 17/144,613

(22) Filed: Jan. 8, 2021

(65) Prior Publication Data
US 2021/0228274 A1    Jul. 29, 2021

Related U.S. Application Data

(60) Provisional application No. 62/964,709, filed on Jan. 23, 2020.

(51) Int. Cl.
*A61B 18/26* (2006.01)
*A61B 17/00* (2006.01)
(Continued)

(52) U.S. Cl.
CPC ........ *A61B 18/26* (2013.01); *A61B 17/00234* (2013.01); *A61B 17/2202* (2013.01); *A61B 2017/00402* (2013.01); *A61B 2018/00511* (2013.01); *A61B 2018/00535* (2013.01); *A61B 2018/00577* (2013.01); *A61B 2018/00982* (2013.01); *A61B 2018/2272* (2013.01);
(Continued)

(58) Field of Classification Search
CPC ...................................................... A61B 18/26
See application file for complete search history.

(56) References Cited

U.S. PATENT DOCUMENTS

| 5,871,462 A * | 2/1999 | Yoder | A61B 17/1644 83/13 |
| 6,752,811 B2 * | 6/2004 | Chu | A61B 17/221 606/114 |

(Continued)

FOREIGN PATENT DOCUMENTS

| CN | 113143456 A | 7/2021 |
| JP | 2021118846 A | 8/2021 |

OTHER PUBLICATIONS

"European Application Serial No. 21150813.0, Extended European Search Report mailed Jun. 9, 2021", 10 pgs.

(Continued)

*Primary Examiner* — Mallika D Fairchild
*Assistant Examiner* — Thien Jason Tran
(74) *Attorney, Agent, or Firm* — Schwegman Lundberg & Woessner, P.A.

(57) ABSTRACT

A reverse retropulsion device can include a lithotripter, a collection passage, and an energy directing device. The lithotripter can be configured to deliver energy to tissue located at a tissue forming region. The collection passage can be positionable at or near the body lumen. The energy directing device can be positionable near the lithotripter and the collection passage. The energy directing device can be configured to propel the tissue toward the collection passage.

20 Claims, 10 Drawing Sheets

(51) Int. Cl.
*A61B 17/22* (2006.01)
*A61B 18/00* (2006.01)
*A61B 18/22* (2006.01)

(52) U.S. Cl.
CPC ... *A61B 2217/005* (2013.01); *A61B 2217/007* (2013.01); *A61B 2218/002* (2013.01); *A61B 2218/007* (2013.01)

(56) References Cited

U.S. PATENT DOCUMENTS

| | | | |
|---|---|---|---|
| 9,421,023 B2 | 8/2016 | Bond et al. | |
| 2002/0068943 A1* | 6/2002 | Chu | A61B 17/221 606/114 |
| 2003/0144672 A1 | 7/2003 | Gellman et al. | |
| 2004/0243123 A1* | 12/2004 | Grasso, III | A61B 18/26 606/41 |
| 2005/0033314 A1 | 2/2005 | Sakurai et al. | |
| 2019/0117309 A1* | 4/2019 | Shelton | A61B 18/26 |
| 2019/0175799 A1 | 6/2019 | Hsu et al. | |
| 2019/0380725 A1 | 12/2019 | Cardinali et al. | |

OTHER PUBLICATIONS

"European Application Serial No. 21150813.0, Response filed Dec. 29, 2021 to Extended European Search Report mailed Jun. 9, 2021", 53 pgs.

* cited by examiner

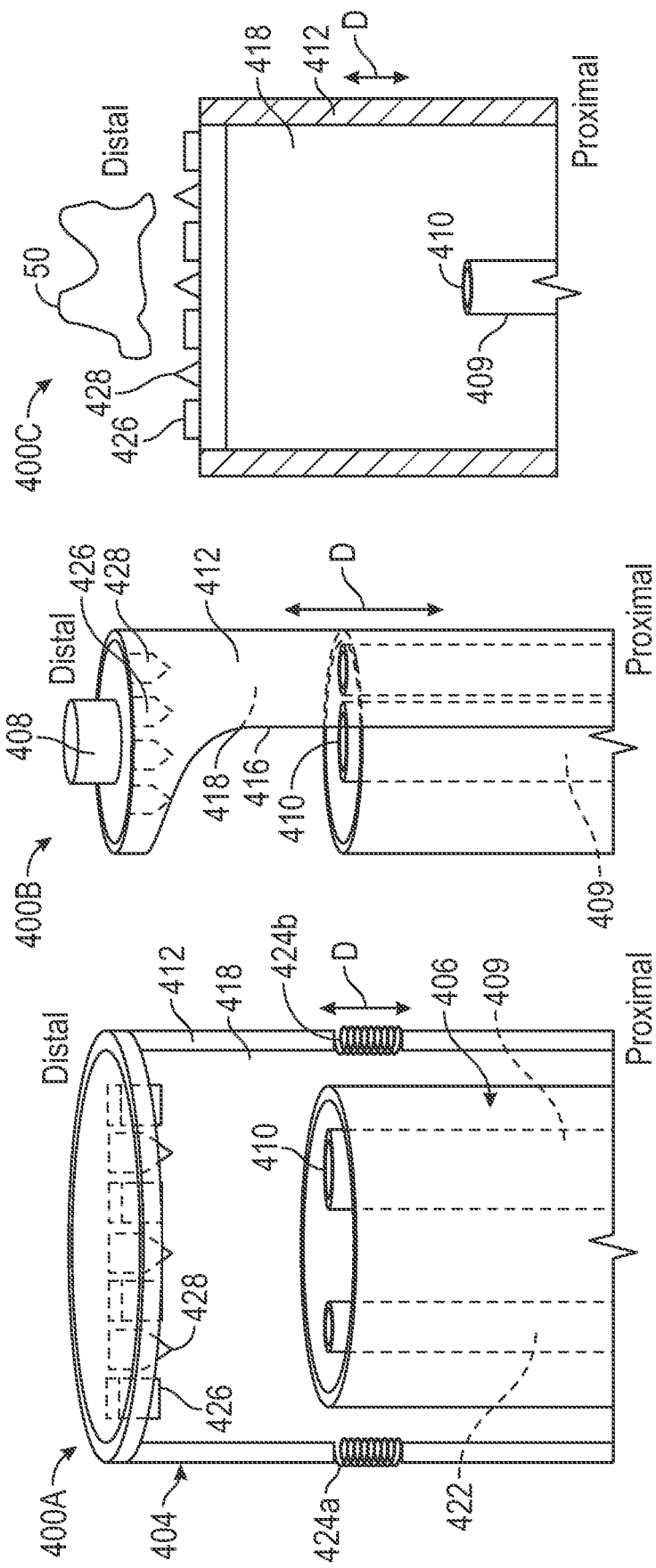

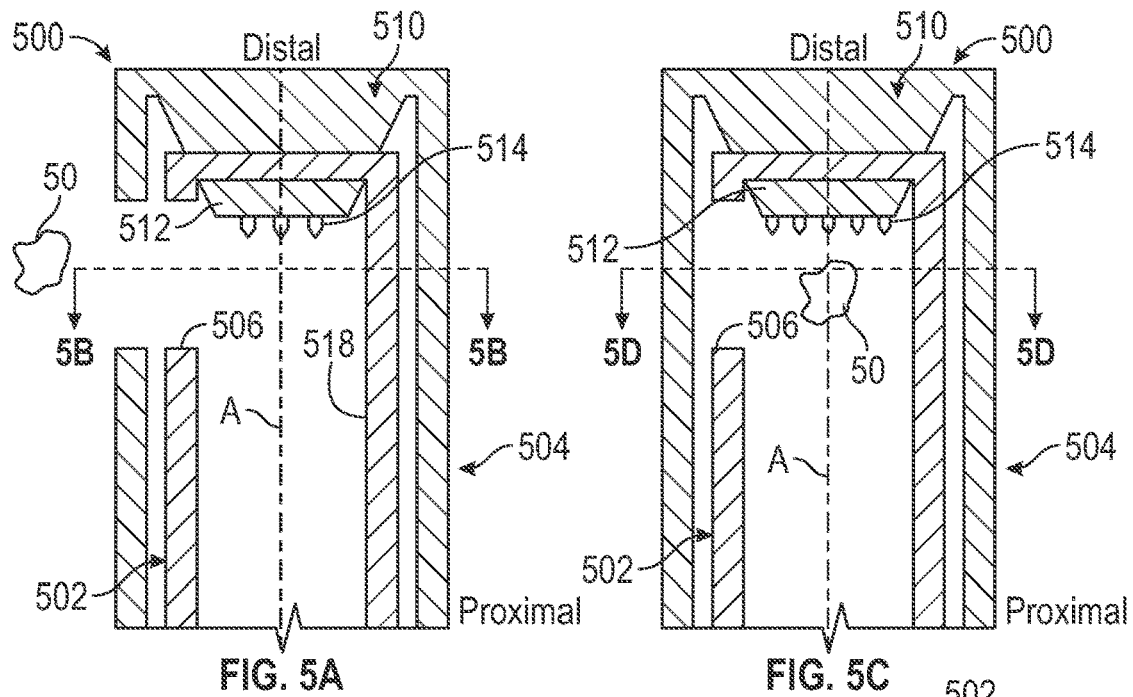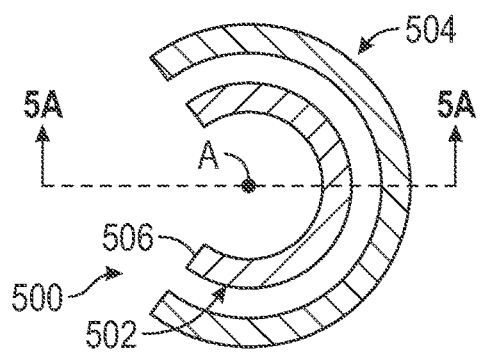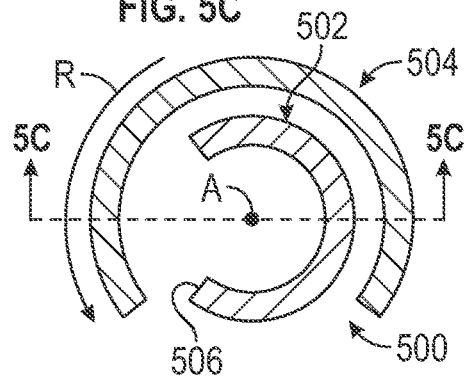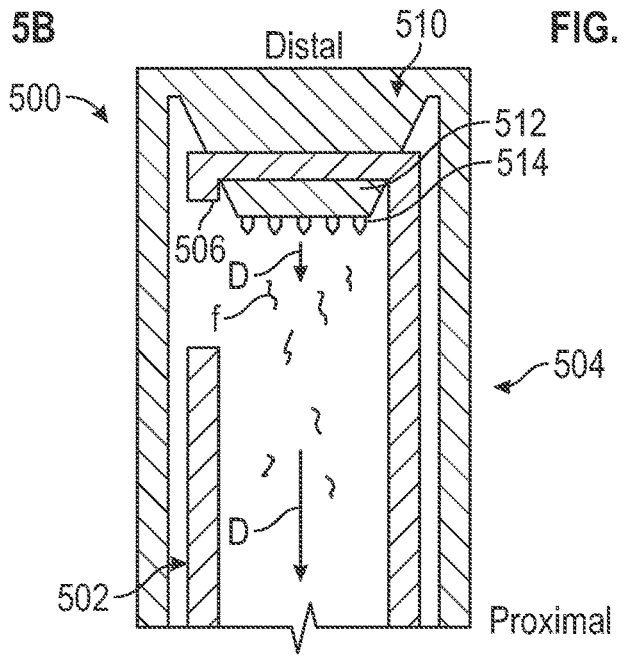

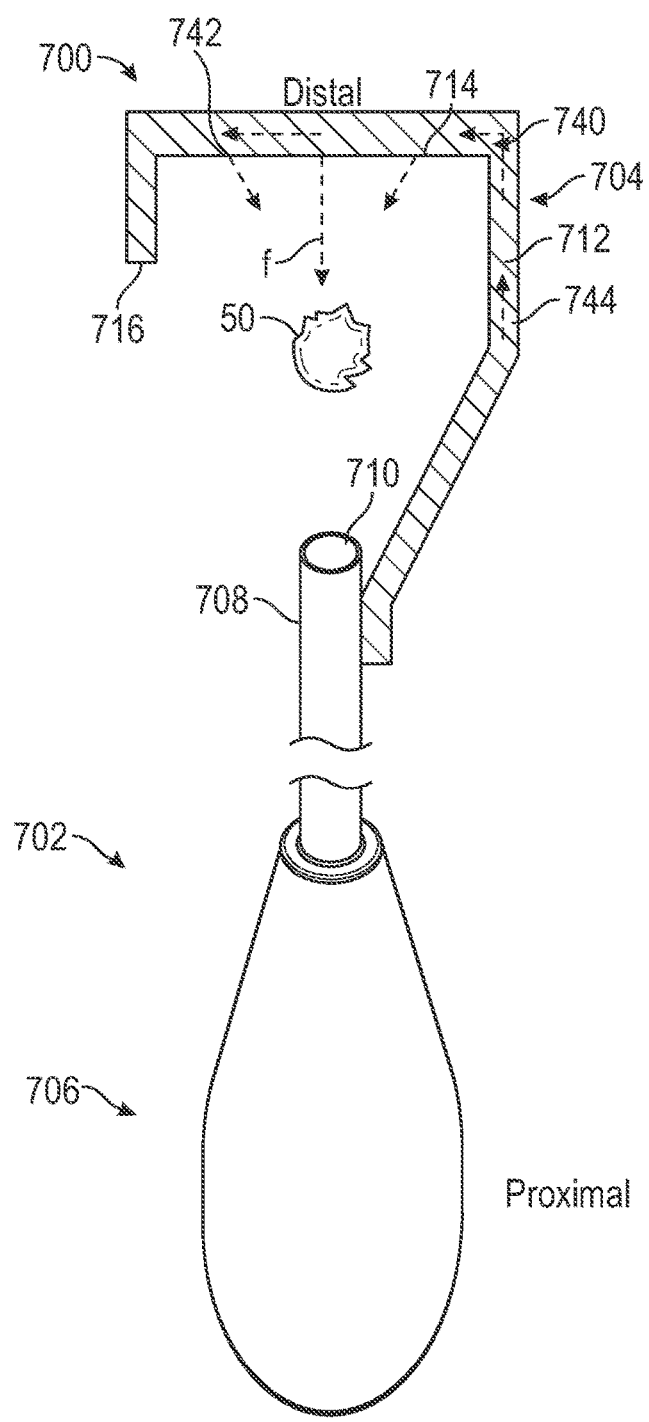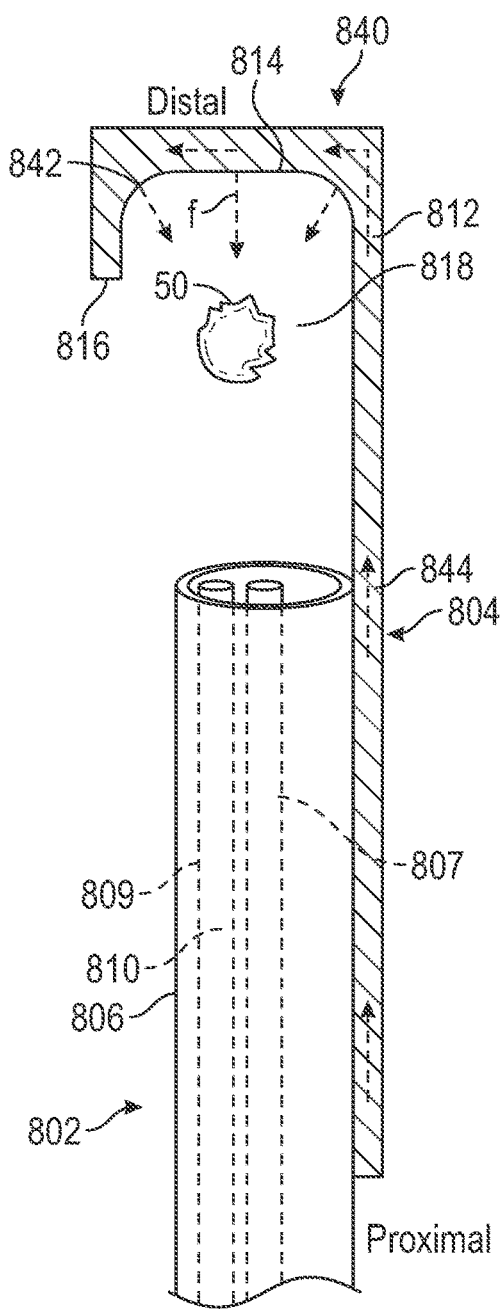
FIG. 7
FIG. 8

REVERSE RETROPULSION LITHOTRIPSY DEVICE

CLAIM OF PRIORITY

This patent application claims the benefit of priority, under 35 U.S.C. Section 119(e), to Jan Pyro, U.S. Patent Application Ser. No. 62/964,709, entitled "REVERSE RETROPULSION LITHOTRIPSY DEVICE," filed on Jan. 23, 2020, which is hereby incorporated by reference herein in its entirety.

BACKGROUND

Tissue can form within organs of the human body such as within a kidney. In some cases, the tissue (such as a stone) is unable pass through the organs naturally and surgical intervention is required to remove the tissue. In many cases, the tissue must be broken into smaller pieces for extraction from a body lumen, such as a kidney or urinary tract. A lithotripsy device can be used to break and extract the tissue. Common modalities of lithotripsy include laser lithotripsy, ultrasonic lithotripsy, and mechanical lithotripsy. In each of these modalities, energy can be delivered to the tissue from the lithotripsy device to break the tissue into smaller pieces for removal.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 4A illustrates a perspective view of a portion of a lithotripsy device, in accordance with at least one example of this disclosure.

FIG. 4B illustrates a perspective view of a portion of a lithotripsy device, in accordance with at least one example of this disclosure.

FIG. 4C illustrates a perspective view of a portion of a lithotripsy device, in accordance with at least one example of this disclosure.

FIG. 5A illustrates a cross-sectional view across indicators 5A-5A of FIG. 5B of a portion of a lithotripsy device in a first condition, in accordance with at least one example of this disclosure.

FIG. 5B illustrates a cross-sectional view across indicators 5B-5B of FIG. 5A of a portion of a lithotripsy device in a first condition, in accordance with at least one example of this disclosure.

FIG. 5C illustrates a cross-sectional view across indicators 5C-5C of FIG. 5D of a portion of a lithotripsy device in a second condition, in accordance with at least one example of this disclosure.

FIG. 5D illustrates a cross-sectional view across indicators 5D-5D of FIG. 5C of a portion of a lithotripsy device in a second condition, in accordance with at least one example of this disclosure.

FIG. 5E illustrates a cross-sectional view of a portion of a lithotripsy device in a third condition, in accordance with at least one example of this disclosure.

FIG. 7 illustrates a perspective view and partial cross-sectional view of a portion of a lithotripsy device, in accordance with at least one example of this disclosure.

FIG. 8 illustrates a perspective view and partial cross-sectional view of a portion of a lithotripsy device, in accordance with at least one example of this disclosure.

DETAILED DESCRIPTION

In each of form of lithotripsy, energy can be delivered to the tissue from the lithotripsy device to break the tissue into smaller pieces for removal of the pieces from the patient; however, the act of applying energy to the tissue from the lithotripsy device can cause retropulsion of the tissue, or movement of the tissue away from the lithotripsy device. Retropulsion of tissue during lithotripsy can complicate further breaking of the tissue and can complicate removal of the tissue and its pieces.

This disclosure provides solutions to the problem of retropulsion by use of reverse retropulsion. That is, pieces of tissue can be directed toward the lithotripsy device, using an energy reversing device, towards a suction device or suction tube. This can help reduce tissue retropulsion and can therefore help save time during a lithotripsy procedure.

In some examples, reverse retropulsion can be achieved by redirecting energy provided by a laser to a backside (or distal side with respect to the instrument) of the tissue to direct the tissue towards the suction tube. In some examples, a cap or reflector can contain the tissue to reflect the tissue and tissue fragments in retropulsion toward the suction tube. In further examples, irrigation fluids can be directed at the tissue to guide the tissue toward the suction tube.

The above discussion is intended to provide an overview of subject matter of the present patent application. It is not intended to provide an exclusive or exhaustive explanation of the invention. The description below is included to provide further information about the present patent application.

Figure 1:
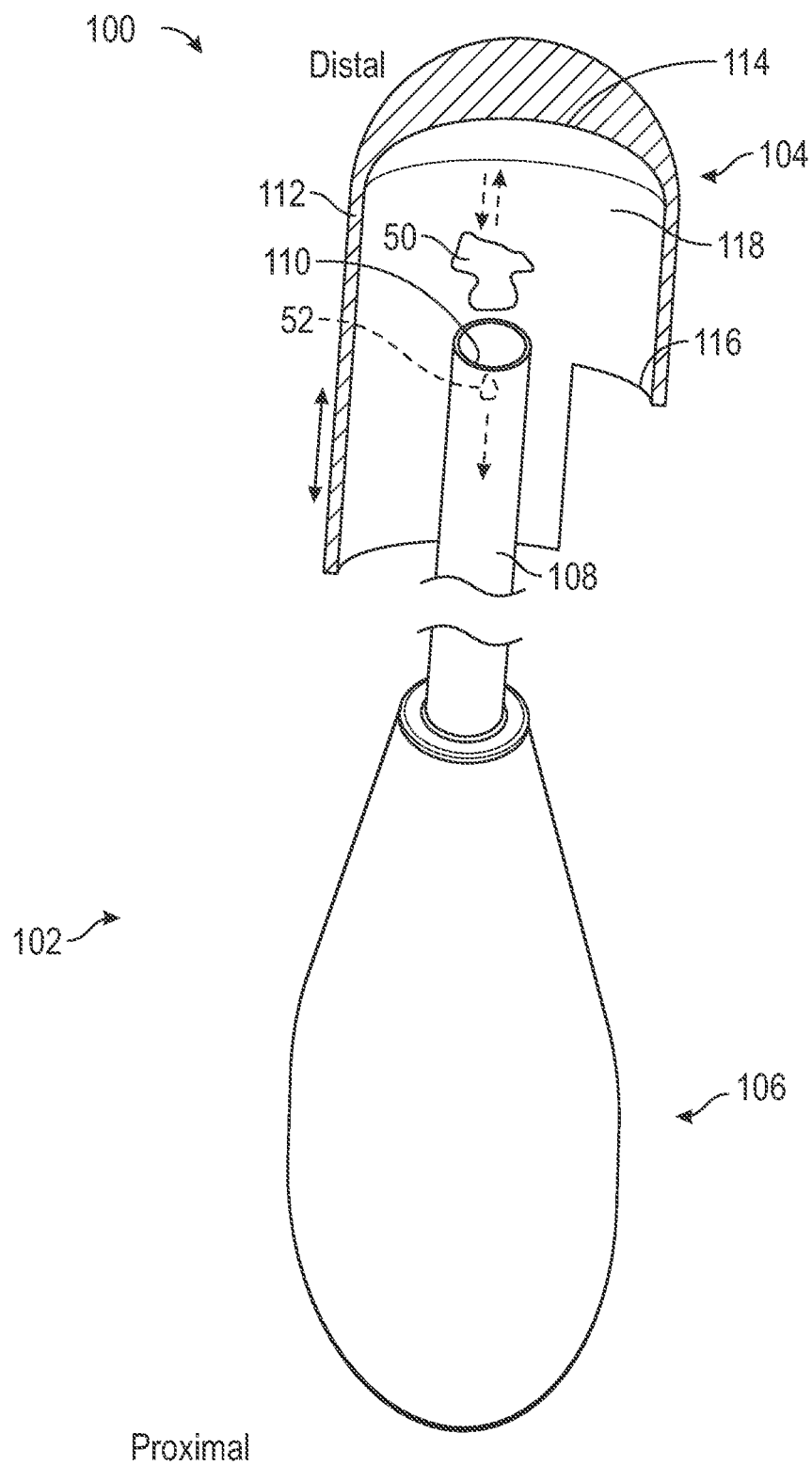
FIG. 1 illustrates a perspective view and partial cross-sectional view of a lithotripsy device, in accordance with at least one example of this disclosure.

FIG. 1 illustrates a perspective and partial cross-sectional view of a lithotripsy device 100. The lithotripsy device 100 can include a lithotripter 102 and a reflector 104. The lithotripter 102 can include a body 106, a probe 108, and a suction lumen 110 (of the probe 108). The reflector 104 can include a body 112, a reflection surface 114, an opening 116, and a cavity 118. Also shown in FIG. 1 are tissue 50, a tissue fragment 52, and orientation indicators Proximal and Distal. The tissue 50 can include any mass in the body lumen, such as soft tissue, hard tissue, calcified tissue, or the like. Stones (such as renal stones or biliary stones) can be a type of hardened tissue and/or may include accreted minerals or tissue, blood and the like. The tissue 50 may be suspended in the body lumen (not attached to any other tissue in the body lumen). In the alternative, the tissue 50 may be substantially (for instance, over a region corresponding to greater than 50% of surface area) suspended, while the remaining portions may be attached to other portion of the body.

The lithotripter 102 can be a lithotripter configured to engage or interact with pieces of tissue of a body lumen of a patient, such as a laser, ultrasonic, electromagnetic, or other lithotripsy device. Lithotripsy can include ablating tissue and the lithotripter 102 can be configured to ablate tissue. In the example shown in FIG. 1, the lithotripter 102 can be an ultrasonic and electromagnetic lithotripter configured for percutaneous use to deliver energy to the tissue 50 to break the tissue 50 into fragments, such as the fragment 52, for removal through the suction lumen 110 of the probe 108.

The body 106 of the lithotripter can be an elongate member positionable external of the body lumen of a patient near the tissue target containing the tissue 50. The body 106 can support the probe 108 and include one or more components configured to deliver energy to the probe 108, such as a piezoelectric stack and a waveguide. The body 106 can further include controls for operation of the lithotripsy device 100. In some examples, the body 106 can be connected to a controller for receipt of power and/or control signals.

The probe 108 of the lithotripter can be an elongate member positionable within a body lumen of a patient near the tissue target containing the tissue 50. A body lumen can be any tissue or stone forming region of the body, such as within a kidney, urinary tract (generally, a renal system of a patient), a biliary tract, or the like. The probe 108 can be configured to deliver energy to the tissue within a portion of the body lumen. The probe 108 can include the suction lumen 110 (or aspiration device) which can extend through the probe 108 and can connect to a suction source at the body 106 or further upstream of the body 106. The suction lumen 110 can be sized to receive fragments of tissue, such as the fragment 52, therethrough for removal from the body lumen.

The reflector 104 can be a cap configured to reflect tissue toward the probe 108. The reflector 104 can be a rigid or semi-rigid member removably or rigidly connectable to the probe 108 at the body 112. In some examples, the reflector 104 can be movably secured to the probe 108 such that the reflector 104 can be extend along a longitudinal axis of the probe 108 or can be rotated with respect to the probe 108, which can help to capture tissue portions of various sizes within the cavity 118 of the reflector 104.

The body 112 can define the reflection surface 114, which can be a curved, arced, or surface of another shape configured to reflect the tissue 50 and fragments thereof toward the probe 108 (and therefore toward the suction lumen 110). The body 112 can also define the opening 116 therein that can be connected to the cavity 118 and can be located proximally of a distal end of the probe 108. The cavity 118 can be sized to container a portion of the lithotripter 102 therein and can receive the tissue 50 therein.

In operation of some examples, the lithotripter 102 can be inserted into the body lumen of the patient near a tissue target, such as near the tissue 50 within a body lumen of the patient. The body 106 can be used to position the tissue 50 through the opening 116 and into the cavity 118 of the reflector body 112 adjacent a distal portion (or tip) of the probe 108. The probe 108 can then be activated to deliver energy to the tissue 50 to break the tissue into fragments. The fragments, such as the fragment 52, can be extracted through the suction lumen 110 and thereby removed from the body lumen of the patient.

During interaction between the probe 108 and the tissue 50, energy applied to the tissue can cause retropulsion, or distal movement of the tissue with respect to the probe 108 and the reflector 104. Because the reflector 104 is positioned distally of the probe 108, the fragments or the tissue 50 can engage the reflection surface 114 and can be redirected proximally for further engagement with the probe 108 until the tissue 50 is completely (or substantially) extracted through the suction lumen 110. The reflector 104 can thereby help to reverse retropulsion for faster destruction and removal of the tissue 50 during a lithotripsy procedure.

Figure 2:
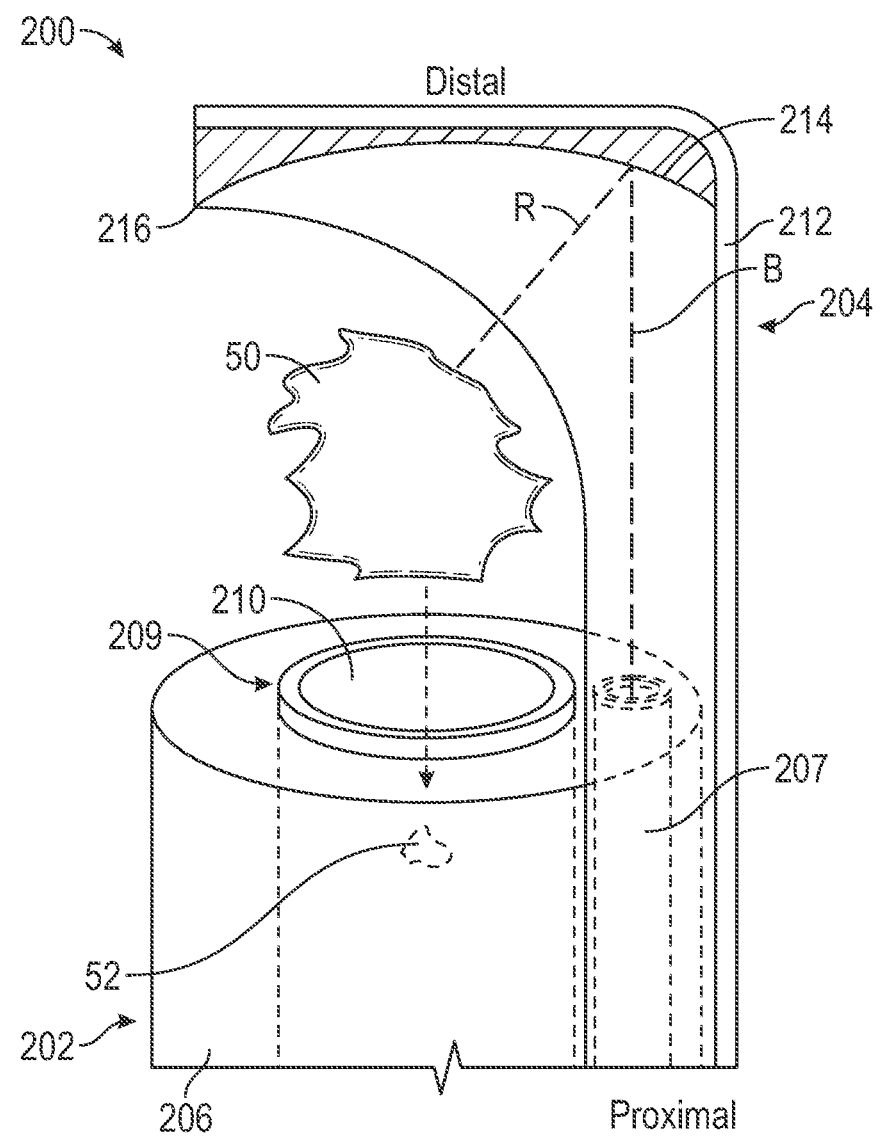
FIG. 2 illustrates a perspective view and partial cross-sectional view of a portion of a lithotripsy device, in accordance with at least one example of this disclosure.

FIG. 2 illustrates a perspective view and partial cross-sectional view of a portion of a lithotripsy device 200. The lithotripsy device 200 can include a lithotripter 202 and a reflector 204. The lithotripter 202 can include a body 206, a laser emitter 207, and a suction cannula 209 (including a lumen 210). The reflector 204 can include a body 212, a reflection surface 214, an opening 216, and a cavity 218. Also shown in FIG. 2 are tissue 50, a beam B, a reflected beam R, and orientation indicators Proximal and Distal.

The lithotripter 202 can be similar to the lithotripter 102 discussed above, except that the lithotripter 202 can use the laser emitter 207 as a modality to deliver energy to the tissue 50 to treat (or break) the tissue 50. The body 206 can be a rigid member in some examples, and can be a flexible member in other examples, such as a flexible shaft of an endoscope (such as a cholangioscope or a ureteroscope). The body 206 can be configured to support the laser emitter 207, the suction cannula 209, and the reflector 204.

The laser emitter 207 can be a portion of a laser, such as an optical fiber, configured to deliver the laser beam B to the tissue 50 to break up the tissue 50 into smaller fragments for extraction. The suction cannula 209 can be a flexible or semi-rigid suction device, such as a tube positionable within the body 206, such as that of an endoscope. The suction lumen 210 can extend through the cannula 209 which can connect to a suction source at the endoscope or further upstream of the endoscope. The suction lumen 210 can be sized to receive fragments of tissue, such as the fragment 52, therethrough for removal from the body lumen.

The reflector 204 can be a cap configured to reflect pieces of tissue toward the suction cannula 209. The reflector 204 can be a flexible or semi-rigid member removably or rigidly connectable to the body 206. In some examples, the reflector 204 can be movably secured to the body 206 such that the reflector 204 can be extend along a longitudinal axis of the body 206 or can be rotated with respect to the body 206, which can help to capture tissue of various sizes within the cavity 218 of the reflector 204. The body 212 can define the opening 216 therein that can be connected to the cavity 218. The cavity 218 can be sized to contain a portion of the lithotripter 202 therein and can receive the tissue 50 therein.

The reflection surface 214 can be a curved, arced, or surface of another shape configured to reflect the tissue 50 and fragments thereof toward the laser emitter 207 (and therefore toward the suction lumen 210). The reflection surface 214 can also be curved (or otherwise shaped) to help direct the beam B toward a distal side of the tissue. In some examples, the reflection surface (and/or other part of the body 212) can include a lining having a reflective coating comprised of one or more of Barium Sulfate, Magnesium Oxide, Polytetrafluoroethylene (PTFE, such as spectralon), a dielectric high reflective coating, a dichroic mirror, or a reflective photonic structure. Such a lining or coating can help increase an efficiency of energy transferred to the tissue 50 via the reflected beam R.

In operation of some examples, the body 206 and reflector 204 can be inserted into the body lumen of the patient at a tissue forming region, such as near the tissue 50 within a body lumen of the patient. In some examples, an endoscope 206 can be used to insert the laser emitter 207 and the reflector 204 into the body lumen. The body 206 can be used to position the tissue 50 through the opening 216 and into the cavity 218 of the reflector body 212 near the suction cannula 209. The laser emitter 207 can then be activated to deliver the beam B which can reflect off the reflection surface 214 of the reflector to create the reflected beam R, which can be directed by the reflection surface 214 to a back or distal portion of the tissue 50. The reflected beam can deliver energy to the tissue 50 to fracture the 50 to create fragments (such as the fragment 52) that are small enough to be extracted from the patient through the suction lumen 210.

Because the reflected beam R is delivered from a distal direction, the tissue 50 can be urged or propelled toward the suction cannula 209 and emitter 207 instead of distally away from the emitter 207 and the cannula 209, helping to limit (or reverse) retropulsion of the tissue 50. Further, if retropulsion of the tissue 50 occurs, it can be limited by contact between the tissue 50 and the body 212 of the reflector 204.

In some examples, the reflection surface 214 can be configured (such as shaped and sized) to direct the beam B towards a center of the cavity 218. In another example, the reflection surface 214 can be configured to direct the beam B towards another (or multiple) portion(s) of the cavity 218, such as over the suction cannula 209. In some examples, the beam B can be delivered to the tissue 50 from a proximal direction.

Figure 3A:
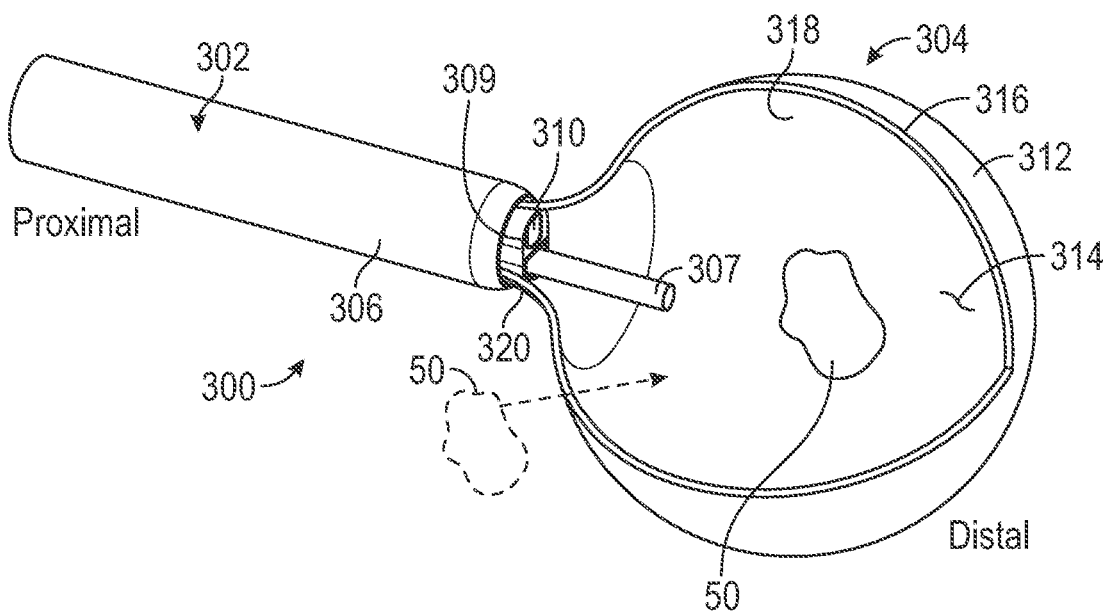
FIG. 3A illustrates a perspective view of a lithotripsy device in a first condition, in accordance with at least one example of this disclosure.
Figure 3B:
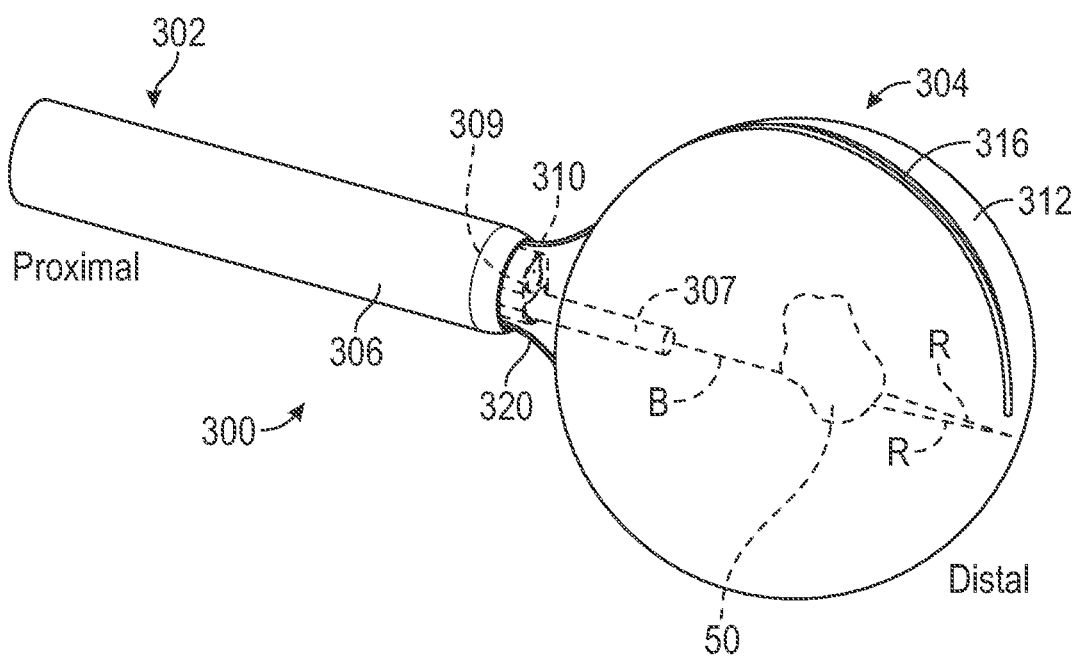
FIG. 3B illustrates a perspective view of a lithotripsy device in a second condition, in accordance with at least one example of this disclosure.

FIG. 3A illustrates a perspective view of a lithotripsy device 300 in an open position. FIG. 3B illustrates a perspective view of a lithotripsy device 300 in a closed position. FIGS. 3A and 3B are discussed below concurrently.

The lithotripsy device 300 can include a lithotripter 302 and a reflector 304. The lithotripter 302 can include a body 306, a laser emitter 307, and a suction cannula 309 (including a lumen 310). The reflector 304 can include a body 312, a reflection surface 314, an opening 316, a cavity 318, and a neck 320. Also shown in FIGS. 3A and 3B are a tissue 50, a beam B, a reflected beam R, and orientation indicators Proximal and Distal.

The lithotripter 302 can be similar to the lithotripter 202 of FIG. 2, except that the laser emitter 307 can extend distally beyond the suction cannula 309. The reflector 304 can be a reflector configured to reflect the beam B emitted by the emitter 307. The reflector 304 can differ in shape from the reflector 202 and in that the reflector 304 can be configured to capture and retain the tissue 50. Any of the previously or later discussed lithotripsy devices can be modified to include such a reflector.

The neck 320 can be a portion of the reflector 304 having a relatively small diameter to connect the body 312 to the lithotripter 302 (such as to the body 306 of the lithotripter 302). The body 312 can extend laterally from the neck 320 as the body 312 extends distally from the neck 320 to form a bulb-shape. In some examples, the body 312 can have other shapes such as a spherical or substantially spherical shape. The body 312 can be operable to open and close the opening 316 such as to capture tissue within the cavity 318. In some examples, the body 312 can be made of more than one piece to allow the body 312 to move between the open position of FIG. 3A and the closed position of FIG. 3B. The reflective surface 314 of the body 312 can be polished and/or can include a coating to increase reflectivity of the reflective surface 314.

In operation of some examples, the body 306 can be used to position the tissue 50 through the opening 316 and into the cavity 318 of the reflector body 312. Once the tissue 50 is within the cavity 318, the body 306 (or another control) can be operated to close the opening 316 of the body 312 to capture the tissue 50 within the cavity 318 of the reflector 304. The laser emitter 307 can then be activated to deliver the beam B which can be delivered to the tissue 50. Retropulsion of the tissue 50 can be prevented by contact between the tissue 50 and the reflector 204.

Also, the beam B can reflect off the reflection surface 314 of the reflector 304 to create the reflected beam R, which can be directed by the reflection surface 314 to a back or distal portion of the tissue 50. The reflected beam R can deliver energy to the tissue 50 to fracture the tissue 50 to create fragments that are small enough to be extracted from the patient through the suction lumen 310. Delivery of the reflected beam R to the distal side of the tissue 50 can also cause reverse retropulsion, helping to direct the tissue 50 to the suction cannula 309. In some examples, the laser can be activated when the body 312 is in the open position, such as if the tissue 50 is too large for the cavity 318 and obstructs closing of the opening 316. Individual or multiple fragments can then be captured by the reflector for completion of lithotripsy and extraction of the tissue 50.

FIG. 4A illustrates a perspective view of a portion of a lithotripsy device 400A, in accordance with at least one example of this disclosure. The lithotripsy device 400A can include an endoscope or body 406, a suction cannula 410, a body 412, an opening 416, a cavity 418, an irrigation supply 422, actuators 424a and 424b, and crush features 426 and 428. Also shown in FIG. 4A are orientation indicators Proximal and Distal and directional arrow D.

The endoscope or body 406 can be a portion of an endoscope (e.g., ureteroscope, cholangioscope, etc.) configured for insertion into a portion of a body lumen for supporting and guiding the suction cannula 410 and the irrigation supply 422. In some examples, the body 406 can be an integral part of the lithotripsy device configured to support the suction cannula 410 and the irrigation supply 422. The irrigation supply 422 can be a tube configured to transport and discharge fluid into the cavity 418 for flushing of tissue fragments out of the cavity 418 through the cannula 410.

The body 412 can be a rigid or semi-rigid member optionally connected to the body 406. The body 412 can form the opening 416 therein, which can be connected to the cavity 418, where the cavity 418 can be sized and shaped to support tissue therein. Actuators 424a and 424b can be connected to the body 412 and configured to move the body 412 in the directions D (proximally and distally). In some examples, the actuators 424a and 424b can be piezoelectric stacks or other drivers configured to oscillate (translate) the body 412 with respect to the body 406.

The crush features 426 and 428 can be connected to a proximal surface of a distal portion of the body and can be directed proximally toward the suction cannula 410. Each of the crush features 426 and 428 can be configured to engage a piece of tissue to fracture or break the tissue. In some examples, the crush features 426 and 428 can be of different shapes and/or oriented in different directions to engage tissues of various shapes and sizes and from various directions to help break up tissues of various shapes and sizes effectively.

FIG. 4B illustrates a perspective view of a portion of a lithotripsy device 400B. The lithotripsy device 400B can be similar to the lithotripsy device 400A discussed above, except that the lithotripsy device 400B can include the probe 408.

The probe 408 can be connected to a distal outside portion of the body 412. The probe 408 can be similar to the probe 108 in that the probe 400 can be connected to one or more components configured to deliver energy to the probe 408, such as a piezoelectric stack and a waveguide. The probe 408 can be positionable within the body lumen of a patient (for example within a renal system) near a tissue-forming target containing tissue and can be configured to deliver energy to the tissue within a portion of the body lumen.

The probe 408 can, for example, be used to fracture or break up tissue that is too large to be positioned within the cavity 418 through the opening 416. Once the tissue is small enough, it can be positioned in the cavity 418 and the crush features 426 and 428 can be used to break the tissue in a more controlled environment, using reverse retropulsion to guide the tissue and fragments of the tissue toward the suction cannula 410 for extraction of the tissue from the body lumen.

FIG. 4C illustrates a perspective view of a portion of a lithotripsy device 400C, in accordance with at least one example of this disclosure. The lithotripsy device 400C can be similar to the lithotripsy device 400A discussed above, except that the lithotripsy device 400C can include externally mounted crush features 426 and 428.

The crush features 426 and 428 can, for example, be used to fracture or break up a tissue that is too large to be positioned within the cavity 418 through the opening 416 and fragments of the tissue can be removed through the suction cannula 410. Once the tissue is small enough, it can be positioned in the cavity 418 and other methods (such as a laser, internal crush features, and/or an internal probe) can be used to break the tissue in a more controlled environment, using reverse retropulsion to guide the tissue and fragments of the tissue toward the suction cannula 410 for extraction of the tissue from the body lumen.

FIG. 5A illustrates a cross-sectional view across indicators 5A-5A of FIG. 5B of a portion of a lithotripsy device 500 in an open position. FIG. 5B illustrates a cross-sectional view across indicators 5B-5B of FIG. 5A of a portion of the lithotripsy device 500 in the open position. FIG. 5C illustrates a cross-sectional view across indicators 5C-5C of FIG. 5D of a portion of the lithotripsy device 500 in a closed position. FIG. 5D illustrates a cross-sectional view across indicators 5D-5D of FIG. 5C of a portion of the lithotripsy device 500 in the closed position. FIG. 5E illustrates a cross-sectional view of a portion of the lithotripsy device 500 in in the closed position while discharging irrigation fluid. FIGS. 5A-5E are discussed below concurrently.

The lithotripsy device 500 can include an inner sleeve 502 and an outer sleeve 504. The inner sleeve 502 can define an opening 506 therein. The outer sleeve 504 can define an opening 508 therein. The lithotripsy device 500 can also include an irrigation system 510 including a header 512 and nozzles 514. Also shown in FIGS. 5A-5E are tissue 50, axis A, fluid f, directional arrows D and R, and orientation indicators Proximal and Distal.

The lithotripsy device 500 can be similar to those discussed above and can include a lithotripter probe for delivery of ultrasonic energy to tissue and/or can include a laser emitter to emit a laser beam toward tissue. In some examples, the lithotripsy device 500 can be connected to any type of lithotripter and in some examples, the lithotripsy device 500 can be connected to an endoscope.

The inner sleeve 502 can be a semi-rigid or flexible member extending along the longitudinal axis A. The inner sleeve 502 can be connected to the outer sleeve 504 and configured to rotate relative to the outer sleeve 504. The inner sleeve 502 can define the opening 506 therein, which can extend through the inner sleeve 502 near a distal end of the inner sleeve 502. Similarly, the outer sleeve 504 can be a semi-rigid or flexible member extending along the longitudinal axis A. The outer sleeve 504 can be connected to the inner sleeve 502 and configured to rotate relative to the outer sleeve 504. In some examples, the inner sleeve 502 and the outer sleeve 504 can be configured to flex together, such as within a cavity of a patient during a procedure.

The outer sleeve 504 can define the opening 508 therein, which can extend through the outer sleeve 540 near a distal end of the outer sleeve 504. The inner sleeve 502 can be connected to a suction device for removal of debris (such as tissue fragments) and fluid (such as the fluid f) from the inner sleeve 502 and the outer sleeve 504. In some examples, the header 512 of the irrigation system 510 can connect the inner sleeve 502 to the outer sleeve 504 to enable rotation of the outer sleeve 504 with respect to the inner sleeve 502.

The irrigation system 510 can be an irrigation system connected to a fluid supply to deliver irrigation fluid to the inner sleeve 502 and the outer sleeve 504. In some examples, the nozzles 514 can be connected to (or formed in) the header 512 and can be configured to discharge irrigation fluid or solution into the cavity and within the inner sleeve 502 (and the outer sleeve 504).

In operation of some examples, the lithotripsy device 500 can be inserted into body lumen near or at a tissue target. Either before or after insertion into the cavity, the outer sleeve 504 can be rotated with respect to the inner sleeve 502 such that the opening 506 aligns with the opening 508, as shown in FIGS. 5A and 5B. When the openings 506 and 508 are in the open position, the device 500 can be used to pass the tissue 50 through the openings 506 and 508 and into a cavity 518 of the inner sleeve 502. Once within the cavity 508, the outer sleeve 504 (or the inner sleeve 502) can be rotated about the axis A in direction R, as shown in FIG. 5D, such that the openings 506 and 508 no longer align, as shown in FIGS. 5C and 5D. In some examples, the outer sleeve 504 (or the inner sleeve 502) can be rotated about the axis A in either direction to open and close the openings 506 and 508.

When the tissue 50 is captured by the outer sleeve 504, lithotripsy can be performed on the tissue 50 and the inner sleeve 502 and the outer sleeve 504 can contain the tissue 50 and its fragments to help limit tissue retropulsion during lithotripsy. Also, when the tissue 50 is captured by the outer sleeve 504, the irrigation system can be enabled such that the nozzles 514 discharge fluid f in the direction D to help direct the tissue 50 and tissue fragments toward the suction device (such as any of the suction devices discussed above, which can be incorporated into the lithotripsy device 500), further helping to reverse retropulsion of the tissue 50 and its fragments during lithotripsy and to help promote relatively fast removal of fragments. Lithotripsy can be performed on the tissue 50 until its fragments are drawn out of the cavity 508 through the suction device. The lithotripsy device 500 can then be removed from the cavity 508.

Figure 6:
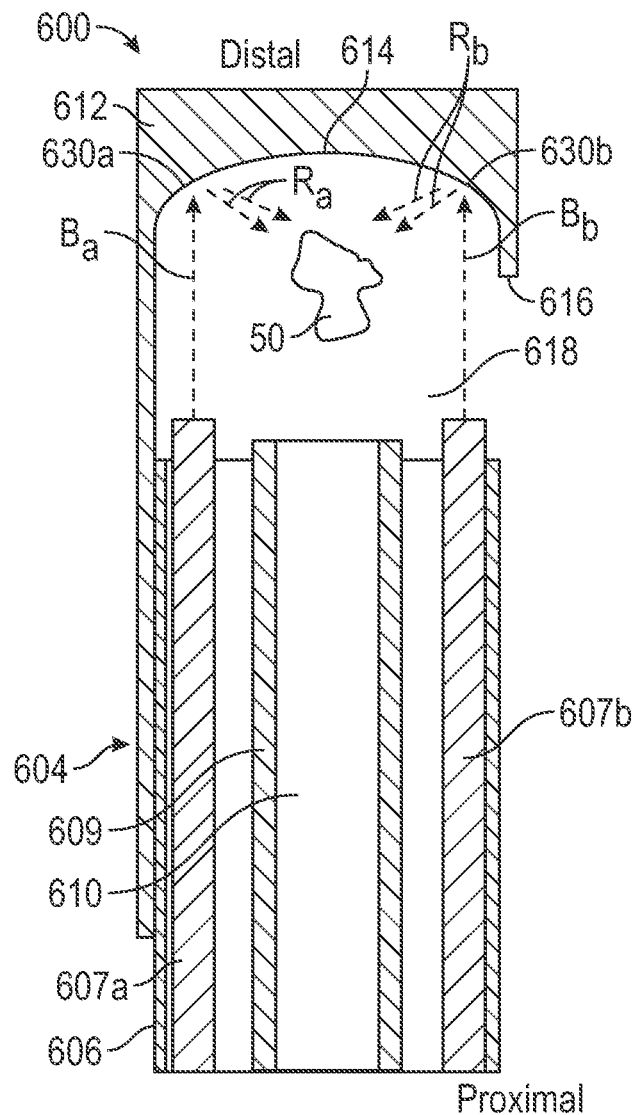
FIG. 6 illustrates a cross-sectional view of a portion of a lithotripsy device, in accordance with at least one example of this disclosure.

FIG. 6 illustrates a cross-sectional view of a portion of a lithotripsy 600 device. The lithotripsy device 600 can include a lithotripter 602, a reflector 604, and an endoscope 606. The lithotripter 602 can include laser emitters 607a and 607b (collectively referred to as laser emitters 607). The lithotripsy device 600 can also include a suction cannula 609 (including a lumen 610). The reflector 604 can include a body 612, a reflection surface 614, an opening 616, and a cavity 618. Also shown in FIG. 6 are tissue 50, beams Ba and Bb, reflected beams Ra and Rb, and orientation indicators Proximal and Distal.

The lithotripsy device 600 can be similar to the lithotripsy device 200 discussed above except that the lithotripsy device 600 can include an endoscope (e.g., ureteroscope or cholangioscope) 606, which can support the laser emitters 607 and the suction cannula 609. Also, the reflector 604 can be attached (such as removably attached) to the endoscope 606. The lithotripsy device 600 can also differ in that it includes two laser emitters 607a and 607b positioned on opposing sides of the cannula 609. Though two laser emitters 607a and 607b are shown, the lithotripsy device can include more laser emitters, such as 3, 4, 5, 6, 7, 8, 9, 10, or the like.

In some examples, the reflection surface 614 can be shaped such that the beams Ba and Bb emitted by the emitters 607a and 607b, respectively, are reflected (shown as reflected beams Ra and Rb, respectively) towards a center portion of the cavity 618 to direct the beams toward the tissue 50. Use of reflected beams Ra and Rb for lithotripsy can help to reverse retropulsion and can help reduce a required time to fracture the tissue 50 for removal through the suction lumen 610. Any of the previously discussed, and/or later-discussed, lithotripsy devices can be modified to include multiple laser emitters.

FIG. 7 illustrates a perspective view and partial cross-sectional view of a portion of a lithotripsy device 700. The lithotripsy device 700 can include a lithotripter 702 and a reflector 704. The lithotripter 702 can include a body 706 and a probe 708 (including a suction lumen 710). The reflector 704 can include a body 712 defining a reflection surface 714 and an opening 716. The reflector 704 can also include an irrigation system 740, which can include nozzles 742. FIG. 7 also shows fluid f and orientation indicators Proximal and Distal.

The lithotripsy device 700 can be similar to the lithotripsy device 100 of FIG. 1, except that the lithotripsy device 700 can include the irrigation system 740, which can include channels 744 routed through the body 712 of the reflector 704, where the channels 744 are configured to support fluid flow therethrough. The channels 744 can be connected to nozzles 742 that can be configured to discharge fluid f from at or near the reflection surface 714.

In operation, the reflector 704 can be positioned at or near a body lumen, such as adjacent the tissue 50. The reflector 704 can be positioned such that the tissue 50 passes through the opening 716 of the body 712 allows the tissue to enter the cavity 718 of the reflector 704. The lithotripter 702 can then be used to fracture the tissue 50, such as by engaging the tissue 50 with the probe 708 to transfer energy to the tissue 50.

During lithotripsy, the irrigation system 740 can be activated and fluid f can be supplied through the channels 744 to the nozzles 742 for discharge toward the suction lumen 710 to help reverse retropulsion of the tissue 50 and to help guide pieces of the tissue 50 toward the lumen 710 for removal of the pieces or fragments of the tissue 50 from the reflector 704 and therefore from the cavity of the patient. Also, when the probe 708 causes retropulsion of the tissue 50 during lithotripsy, the irrigation system 740 can help propel, or urge, the tissue 50 proximally toward the probe 708, which can help reduce time required for fracture and removal of the tissue 50. Any of the previously discussed, and/or later-discussed, lithotripsy devices can be modified to include such an irrigation system.

FIG. 8 illustrates a perspective view and partial cross-sectional view of a portion of a lithotripsy device 800. The lithotripsy device 800 can include a lithotripter 802, a reflector 804, and an endoscope 806. The lithotripter 802 can include a laser emitter 807. The lithotripsy device 800 can also include a suction cannula 809 (including a lumen 810). The reflector 804 can include a body 812, a reflection surface 804, an opening 816, and a cavity 818. The reflector 804 can also include an irrigation system 840, which can include nozzles 842 and channels 844. FIG. 8 also shows fluid f and orientation indicators Proximal and Distal.

The lithotripsy device 800 can be similar to the lithotripsy device 200 of FIG. 2, except that the lithotripsy device 800 can include the irrigation system 840, which can include channels 844 routed through the reflector 804 and the channels 844 can be configured to support fluid flow therethrough. The channels 844 can be connected to nozzles 842 such that the nozzles 842 can discharge fluid f from at or near the reflection surface 814.

In operation, the reflector 804 can be positioned at or near a tissue forming region, such as adjacent the tissue 50, and the reflector 804 can be positioned such that the tissue 50 passes through the opening 816 of the body 812 allowing the tissue to enter the cavity 818 of the reflector 804. The lithotripter 802 can then be used to fracture the tissue 50, such as by emitting a beam from the emitter 807 (which can be reflected by the reflection surface 814) to the tissue 50.

During lithotripsy, the irrigation system 840 can be activated and fluid f can be supplied through the channels 844 to the nozzles 842 for discharge toward the suction lumen 810 to help reverse retropulsion of the tissue 50 and to help guide pieces of the tissue 50 toward the lumen 810 for removal of the pieces or fragments of the tissue 50 from the reflector 804 and therefore from the cavity of the patient. Any of the previously discussed, or later-discussed, lithotripsy devices can be modified to include such an irrigation system.

Figure 9A:
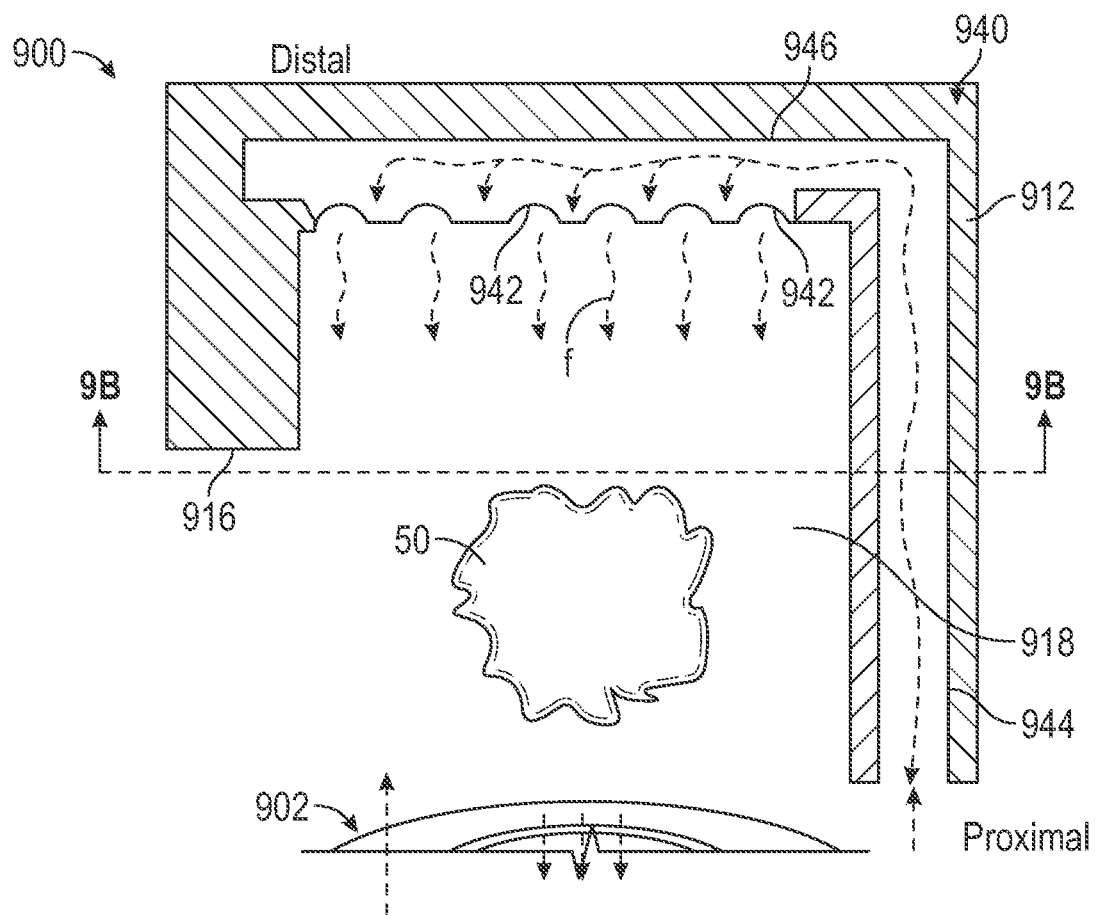
FIG. 9A illustrates a cross-sectional view across indicators 9A-9A of FIG. 9B of a portion of a lithotripsy device, in accordance with at least one example of this disclosure.
Figure 9B:
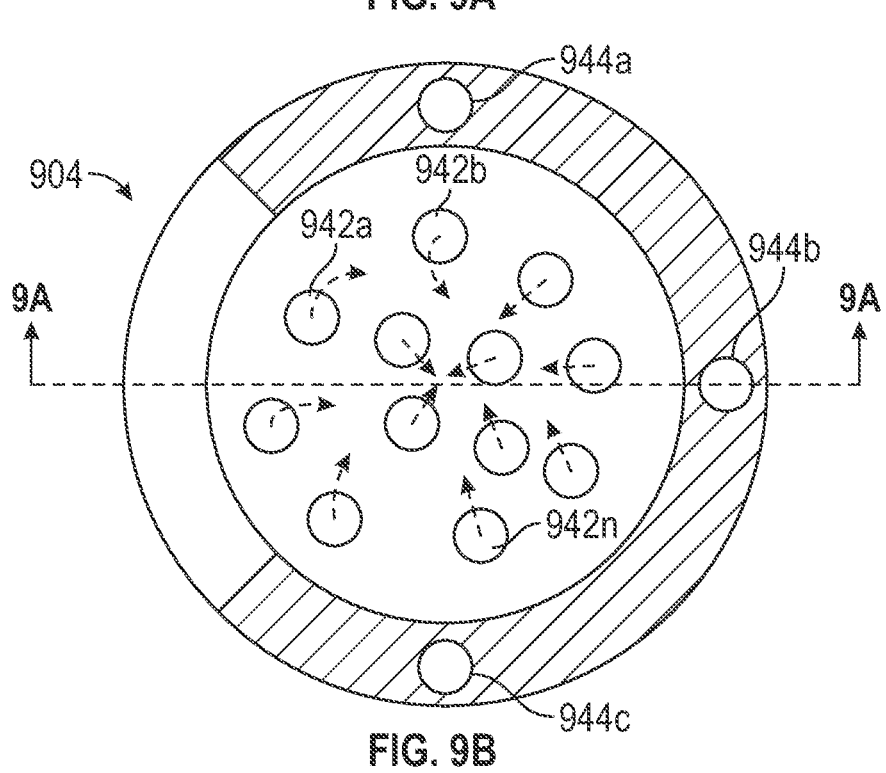
FIG. 9B illustrates a cross-sectional view across indicators 9B-9B of FIG. 9A of a portion of a lithotripsy device, in accordance with at least one example of this disclosure.

FIG. 9A illustrates a cross-sectional view across indicators 9A-9A of FIG. 9B of a portion of a lithotripsy device 900. FIG. 9B illustrates a cross-sectional view across indicators 9B-9B of FIG. 9A of a portion of the lithotripsy device 900. FIGS. 9A and 9B are discussed below concurrently.

The lithotripsy device 900 can include a lithotripter 902 and a reflector 904. The lithotripter 902 can be similar to any of those discussed above. The reflector 904 can include a body 912 defining an opening 916 and a cavity 918. The reflector 904 can also include an irrigation system 940, which can include nozzles 942a-942n (collectively referred to as the nozzles 942), channels 944a-944c (collectively referred to as the channels 944), and a header 946. FIGS. 9A and 9B also show fluid f and orientation indicators Proximal and Distal.

The channels 944 can be routed (individually, for example) through the body 912 and can connected to the header 946 which can be connected to the nozzles 942. During a lithotripsy procedure, fluid f can be provided to the channels 944 and to the headers 946 for distribution to the nozzles 942. The nozzles 942 can be shaped, positioned, and/or configured to discharge fluid f therefrom proximally to propel tissue proximally, or toward a suction device of the lithotripter 902. Any of the previously discussed, or later-discussed, lithotripsy devices can be modified to include such an irrigation system.

Figure 10:
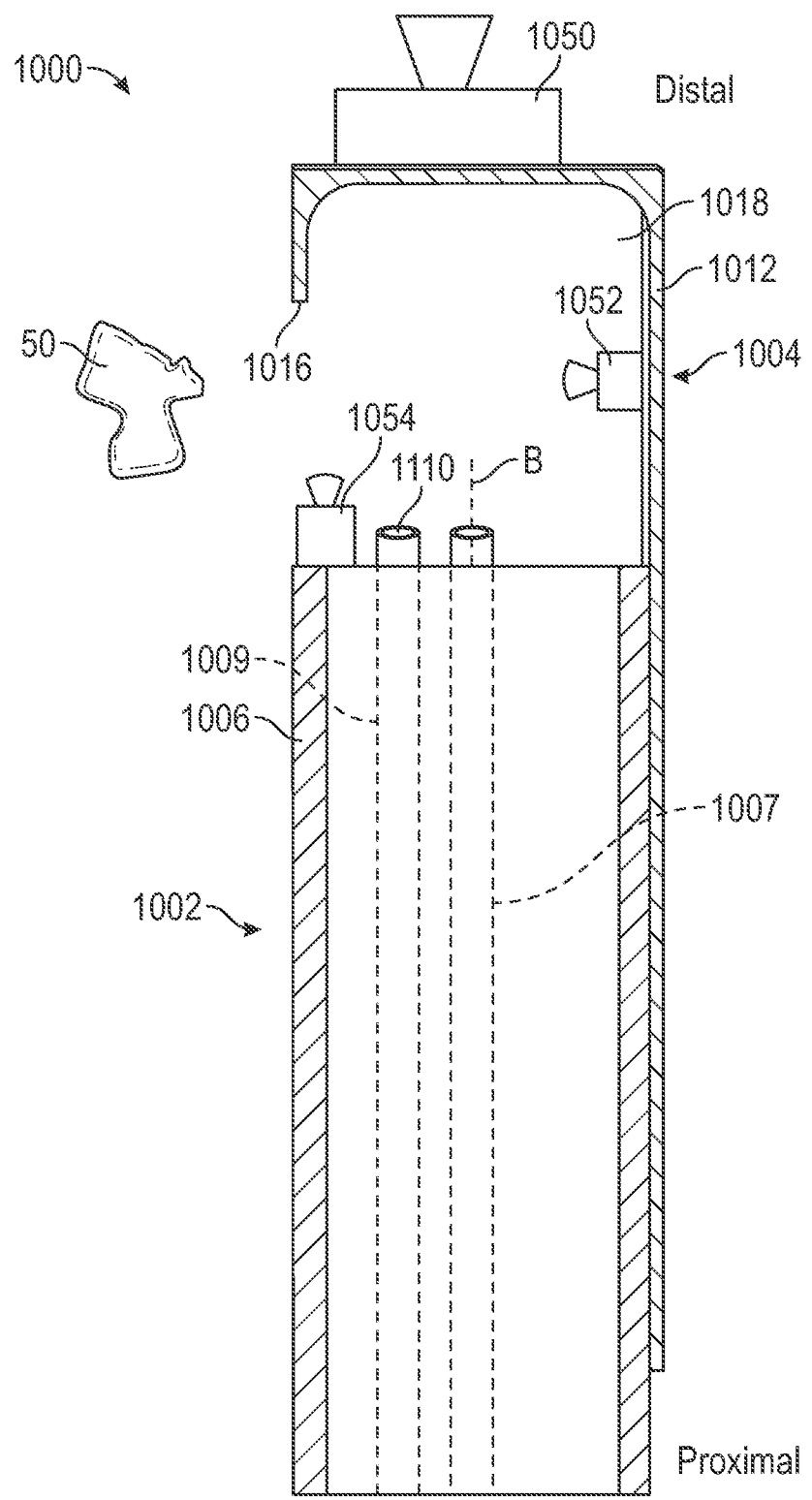
FIG. 10 illustrates a cross-sectional view of a portion of a lithotripsy device, in accordance with at least one example of this disclosure.

FIG. 10 illustrates a cross-sectional view of a portion of a lithotripsy device 1000. The lithotripsy device 1000 can include a lithotripter 1002, a reflector 1004, an endoscope 1006, a distal camera 1050, a reflector camera 1052, and a scope camera 1054. The lithotripter 1002 can include a laser emitter 1007. The lithotripsy device 1000 can also include a suction cannula 1009 (including a lumen 1010). The reflector 1004 can include a body 1012, a reflection surface 1014, an opening 1016, and a cavity 1018. FIG. 10 also shows orientation indicators Proximal and Distal.

The lithotripsy device 1000 can be similar to those discussed above, except that the lithotripsy device 1000 can include the distal camera 1050, the reflector camera 1052, and the scope camera 1054.

Each of the distal camera 1050, the reflector camera 1052, and the scope camera 1054 can be digital camera devices (or an imaging device) configured to produce an optical or image signal based on imagery around the lithotripsy device. The distal camera 1050 can be connected to a distal portion of the reflector 1004 and positioned and configured to have a field of view in front of, or distal of, the reflector 1004. The reflector camera 1052 can be connected to an internal portion of the reflector 1004 and can be positioned and configured to have a field of view of the opening 1016. The scope camera 1054 can be connected to a distal portion of the scope (such as near the opening 1016) and can be positioned and configured to have a field of view of the opening 1016 and the reflection surface 1014.

In operation of some examples, the lithotripsy device can be inserted into the cavity 1018. The distal camera 1050 on the reflector 1004 can be used to position the reflector near tissue within a tissue target, such as near the opening 1016 of the body. Then, the reflector camera 1052 and the scope camera 1054 can each be used to guide the tissue through the opening 1016 into the cavity 1018 and can further be used to position the tissue within the cavity before and during lithotripsy of the tissue.

Though the lithotripsy device 1000 is shown as including three cameras, fewer or more cameras can be included, such as 1, 2, 4, 5, 6, 7, 8, 9, 10, or the like.

Figure 11:
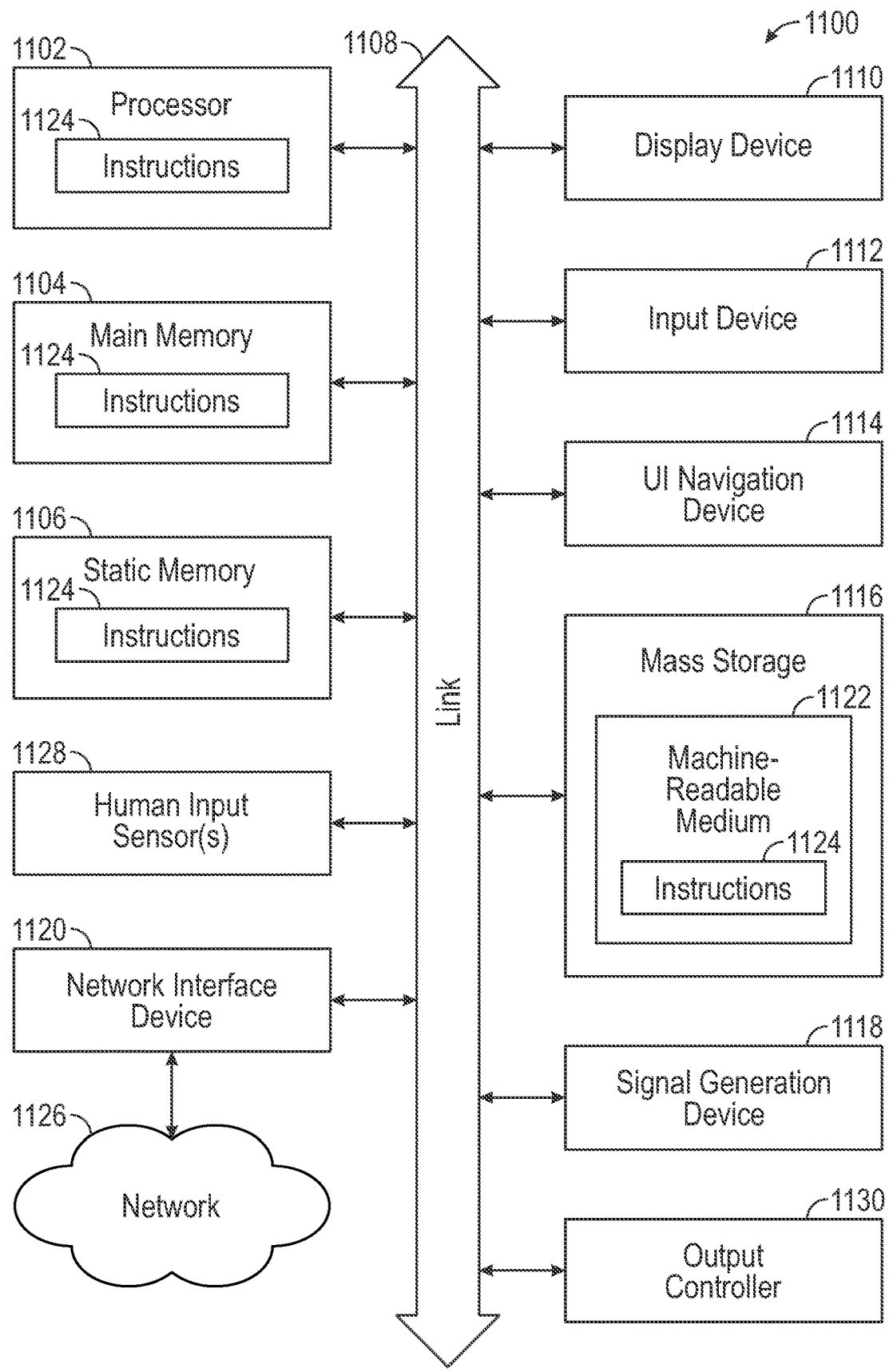
FIG. 11 illustrates a schematic view of a lithotripsy system, in accordance with at least one example of this disclosure.

FIG. 11 illustrates a block diagram of a lithotripsy system 1100 which any one or more of the previous techniques may be performed or facilitated by. The computer system 1100 specifically may be used in connection with facilitating the operations of the lithotripsy devices 100-1000 described or referred to herein. For example, the computer system 1100 can be connected to the distal camera 1050, the reflector camera 1052, the scope camera 1054, and the emitter 1007.

In alternative embodiments, the system 1100 can operate as a standalone device or may be connected (e.g., networked) to other machines. In a networked deployment, the machine can operate in the capacity of either a server or a client machine in server-client network environments, or it can act as a peer machine in peer-to-peer (or distributed) network environments. The machine can be a personal computer (PC), a tablet PC, a smartphone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 1100 can include a processor 1102 (e.g., a central processing unit (CPU), a graphics processing unit (GPU) or both), a main memory 1104 and a static memory 1106, which communicate with each other via a link 1108 (e.g., an interlink, bus, etc.). The computer system 1100 can also include a video display unit 1110, an alphanumeric input device 1112 (e.g., a keyboard), and a user interface (UI) navigation device 1114 (e.g., a mouse). In an example, the video display unit 1110, input device 1112 and UI navigation device 1114 are a touch screen display. The computer system 1100 can additionally include a storage device 1116 (e.g., a drive unit), a signal generation device 1118 (e.g., a speaker), and a network interface device 1120 which can operably communicate with a communications network 1126 using wired or wireless communications hardware. The computer system 1100 can further include one or more human input sensors 1128 configured to obtain input (including non-contact human input) in accordance with input recognition and detection techniques. The human input sensors 1128 may include a camera, microphone, barcode reader, RFID reader, near field communications reader, or other sensor producing data for purposes of input. The computer system 1100 can further include an output controller 1130, such as a serial (e.g., universal serial bus (USB), parallel, or other wired or wireless (e.g., infrared (IR)) connection to communicate or control one or more peripheral devices (e.g., a printer, card reader, etc.).

The storage device 1116 can include a machine-readable medium 1122 on which is stored one or more sets of data structures or instructions 1124 (e.g., software) embodying or utilized by any one or more of the methodologies or functions described herein. The instructions 1124 can also reside, completely or at least partially, within the main memory 1104, static memory 1106, and/or within the processor 1102 during execution thereof by the computer system 1100, with the main memory 1104, static memory 1106, and the processor 1102 also constituting machine-readable media.

While the machine-readable medium 1122 is illustrated in an example embodiment to be a single medium, the term "machine-readable medium" can include a single medium or multiple media (e.g., a centralized or distributed database, and/or associated caches and servers) that store the one or more instructions 1124. The term "machine-readable medium" shall also be taken to include any tangible medium (e.g., a non-transitory medium) that is capable of storing, encoding or carrying instructions for execution by the computer system 1100 and that cause the computer system 1100 to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1124 can further be transmitted or received over a communications network 1126 using a transmission medium via the network interface device 1120 utilizing any one of a number of well-known transfer protocols (e.g., frame relay, internet protocol (IP), transmission control protocol (TCP), user datagram protocol (UDP), hypertext transfer protocol (HTTP)). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the computing system 1100, and includes digital or analog communications signals or other intangible medium to facilitate communication of such software.

As an additional example, computing embodiments described herein may be implemented in one or a combination of hardware, firmware, and software. Embodiments may also be implemented as instructions stored on a computer-readable storage device, which can be read and executed by at least one processor to perform the operations described herein. A computer-readable storage device may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media.

It should be understood that the functional units or capabilities described in this specification may have been referred to or labeled as components or modules, in order to more particularly emphasize their implementation independence. Component or modules can be implemented in any combination of hardware circuits, programmable hardware devices, other discrete components. Components or modules can also be implemented in software for execution by various types of processors. An identified component or module of executable code can, for instance, comprise one or more physical or logical blocks of computer instructions, which may, for instance, be organized as an object, procedure, or function. Nevertheless, the executables of an identified component or module need not be physically located together, but can comprise disparate instructions stored in different locations which, when joined logically together, comprise the component or module and achieve the stated purpose for the component or module. Indeed, a component or module of executable code may be a single instruction, or many instructions, and may even be distributed over several different code segments, among different programs, and across several memory devices.

Similarly, operational data can be identified and illustrated herein within components or modules, and may be embodied in any suitable form and organized within any suitable type of data structure. The operational data can be collected as a single data set, or may be distributed over different locations including over different storage devices, and may exist, at least partially, merely as electronic signals on a system or network. The components or modules can be passive or active, including agents operable to perform desired functions.

Notes and Examples

The following, non-limiting examples, detail certain aspects of the present subject matter to solve the challenges and provide the benefits discussed herein, among others.

Example 1 is a reverse retropulsion device comprising: a lithotripter configured to deliver energy to tissue located at a tissue forming region; a collection passage positionable at or near the body lumen; and an energy directing device positionable near the lithotripter and the collection passage, the energy directing device configured to propel the tissue toward the collection passage.

In Example 2, the subject matter of Example 1 optionally includes wherein the lithotripter comprises a laser emitter operable to deliver light energy to the tissue.

In Example 3, the subject matter of Example 2 optionally includes wherein the energy directing device comprises a reflector connected to the lithotripter and positionable to reflect the light energy to propel the tissue toward the collection passage.

In Example 4, the subject matter of Example 3 optionally includes wherein the lithotripter comprises a second laser emitter operable to deliver light energy to the reflector.

In Example 5, the subject matter of any one or more of Examples 2-4 optionally include wherein the reflector comprises a reflective coating comprised of one or more of Barium Sulfate, Magnesium Oxide, a dielectric highly reflective coating, Polytetrafluoroethylene, a dichroic mirror, a reflective photonic structure.

In Example 6, the subject matter of any one or more of Examples 1-5 optionally include wherein the lithotripter is an ultrasonic lithotripter.

In Example 7, the subject matter of any one or more of Examples 1-6 optionally include wherein the energy directing device comprises a reflector connected to the lithotripter, the reflector configured to reflect portions of the tissue toward the collection passage.

In Example 8, the subject matter of any one or more of Examples 1-7 optionally include wherein the energy directing device comprises a reflector connected to an endoscope, the reflector configured to reflect portions of the tissue toward the collection passage.

In Example 9, the subject matter of any one or more of Examples 1-8 optionally include a capture device connected to the lithotripter and positionable at or near the body lumen, the capture device operable to move between an open position to capture the tissue and a closed position to retain the tissue therein.

In Example 10, the subject matter of Example 9 optionally includes wherein the energy directing device includes the capture device.

In Example 11, the subject matter of Example 10 optionally includes wherein the capture device includes a reflective inner surface to reflect light delivered by a laser of the lithotripter to the tissue within the capture device.

In Example 12, the subject matter of any one or more of Examples 9-11 optionally include the capture device comprising: an inner sleeve defining an opening to receive the tissue into the sleeve proximate the collection passage and the lithotripter; and an outer sleeve connected to the inner sleeve, the outer sleeve moveable to open and close the opening.

In Example 13, the subject matter of Example 12 optionally includes wherein the outer sleeve is rotatable with respect to the inner sleeve about an axis common to the outer sleeve and the inner sleeve to open and close the opening of the inner sleeve.

In Example 14, the subject matter of any one or more of Examples 1-13 optionally include wherein the energy directing device includes an outer sleeve translatable with respect to the lithotripter to apply a force to the tissue and to propel the tissue toward the collection passage.

In Example 15, the subject matter of Example 14 optionally includes wherein the energy directing device includes a plurality of projections extending proximally from a distal portion of the outer sleeve, the projections configured to apply the force to the tissue to break the tissue.

In Example 16, the subject matter of any one or more of Examples 1-15 optionally include wherein the energy directing device is configured to discharge irrigation fluid toward the collection passage.

In Example 17, the subject matter of Example 16 optionally includes wherein the energy directing device includes an irrigation device connected to a distal portion of the energy directing device, the irrigation device configured to discharge fluid toward the collection passage.

In Example 18, the subject matter of Example 17 optionally includes wherein the irrigation device includes a plurality of jets to discharge fluid to propel the tissue toward the collection passage.

In Example 19, the subject matter of any one or more of Examples 1-18 optionally include an imaging device connected to an outer portion of the energy directing device.

In Example 20, the subject matter of any one or more of Examples 1-19 optionally include wherein the body lumen is a renal target and the tissue is a stone.

Example 21 is a reverse retropulsion device for performing a lithotripsy procedure, the reverse retropulsion comprising: a lithotripter configured to transfer energy to tissue at a body lumen; a collection passage positionable at or near the body lumen near the energy delivery device; and a reflector positionable at or near the body lumen distal of the lithotripter, the reflector configured to direct energy from the lithotripter to the tissue to propel the tissue toward the collection passage.

In Example 22, the subject matter of Example 21 optionally includes wherein the lithotripter comprises a laser emitter operable to deliver light energy to the tissue.

In Example 23, the subject matter of Example 22 optionally includes wherein reflector is connected to the lithotripter.

In Example 24, the subject matter of Example 23 optionally includes wherein the lithotripter comprises a second laser emitter operable to deliver light energy to the reflector.

In Example 25, the subject matter of Example 24 optionally includes wherein reflector includes a curved reflection surface to focus reflected light toward the collection passage.

In Example 26, the subject matter of any one or more of Examples 22-25 optionally include wherein the reflector comprises a reflective coating comprised of one or more of Barium Sulfate, Magnesium Oxide, a dielectric HR coating, a dichroic mirror, a reflective photonic structure.

Example 27 is a reverse retropulsion device for performing a lithotripsy procedure, the reverse retropulsion comprising: a lithotripter configured to transfer energy to tissue within the cavity at a body lumen; a collection passage positionable at or near the body lumen near the energy delivery device; and an irrigation device positionable at or near the body lumen distal of the lithotripter, the irrigation device configured to direct fluid to propel the tissue toward the collection passage.

In Example 28, the apparatuses or method of any one or any combination of Examples 1-27 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:
1. A reverse retropulsion device comprising:
a lithotripter configured to deliver energy to tissue located at a tissue forming region;

a collection passage positionable at or near a body lumen; and an energy directing device comprising:
a body connected to the lithotripter and the collection passage; and
a reflector connected to the body, the reflector separated from and located distal of the lithotripter and the collection passage, the reflector configured to propel the tissue toward the collection passage, and the reflector configured to engage portions of the tissue to reflect portions of the tissue toward the collection passage.

2. The reverse retropulsion device of claim 1, wherein the lithotripter comprises a laser emitter operable to deliver light energy to the tissue.

3. The reverse retropulsion device of claim 2, wherein the reflector is configured to reflect the light energy to propel the tissue toward the collection passage.

4. The reverse retropulsion device of claim 3, wherein the lithotripter comprises a second laser emitter operable to deliver light energy to the reflector.

5. The reverse retropulsion device of claim 2, wherein the reflector comprises a reflective coating comprised of one or more of Barium Sulfate, Magnesium Oxide, a dielectric highly reflective coating, Polytetrafluoroethylene, a dichroic mirror, a reflective photonic structure.

6. The reverse retropulsion device of claim 1, wherein the lithotripter is an ultrasonic lithotripter.

7. The reverse retropulsion device of claim 1, wherein the reflector is connected to an endoscope, the reflector configured to reflect portions of the tissue toward the collection passage.

8. The reverse retropulsion device of claim 1, further comprising:
a capture device connected to the lithotripter and positionable at or near the body lumen, the capture device operable to move between an open position to capture the tissue and a closed position to retain the tissue therein.

9. The reverse retropulsion device of claim 8, wherein the energy directing device includes the capture device.

10. The reverse retropulsion device of claim 9, wherein the capture device includes a reflective inner surface to reflect light delivered by a laser of the lithotripter to the tissue within the capture device.

11. The reverse retropulsion device of claim 8, the capture device comprising:
an inner sleeve defining an opening to receive the tissue into the sleeve proximate the collection passage and the lithotripter; and
an outer sleeve connected to the inner sleeve, the outer sleeve moveable to open and close the opening.

12. The reverse retropulsion device of claim 11, wherein the outer sleeve is rotatable with respect to the inner sleeve about an axis common to the outer sleeve and the inner sleeve to open and close the opening of the inner sleeve.

13. The reverse retropulsion device of claim 1, wherein the energy directing device includes an outer sleeve translatable with respect to the lithotripter to apply a force to the tissue and to propel the tissue toward the collection passage.

14. The reverse retropulsion device of claim 13, wherein the energy directing device includes a plurality of projections extending proximally from a distal portion of the outer sleeve, the projections configured to apply the force to the tissue to break the tissue.

15. The reverse retropulsion device of claim 1, wherein the energy directing device is configured to discharge irrigation fluid toward the collection passage.

16. The reverse retropulsion device of claim 15, wherein the energy directing device includes an irrigation device connected to a distal portion of the energy directing device, the irrigation device configured to discharge fluid toward the collection passage.

17. The reverse retropulsion device of claim 16, wherein the irrigation device includes a plurality of jets to discharge fluid to propel the tissue toward the collection passage.

18. A reverse retropulsion device comprising:
a lithotripter configured to deliver energy to tissue located at a tissue forming region;
a collection passage positionable at or near a lumen; and
an energy directing device connected to the lithotripter, the energy directing device located distal of and spaced apart from the lithotripter and the collection passage, the energy directing device configured to propel the tissue toward the collection passage, and the energy directing device including an outer sleeve translatable with respect to the lithotripter to apply a force to the tissue and to propel the tissue toward the collection passage.

19. A reverse retropulsion device comprising:
a lithotripter configured to deliver energy to tissue located at a tissue forming region;
a collection passage positionable at or near a lumen; and
an energy directing device connected to the lithotripter, the energy directing device located distal of and separated away from the lithotripter and the collection passage, the energy directing device configured to propel the tissue toward the collection passage, and the energy directing device including a plurality of projections extending proximally from a distal portion of an outer sleeve, the projections configured to apply force to the tissue to break the tissue.

20. The reverse retropulsion device of claim 19, wherein the energy directing device includes an irrigation device connected to a distal portion of the energy directing device, the irrigation device configured to discharge fluid toward the collection passage.

* * * * *